United States Patent [19]
Campbell et al.

[11] Patent Number: 5,837,537
[45] Date of Patent: Nov. 17, 1998

[54] δ-SARCOGLYCAN NUCLEIC ACID SEQUENCES

[75] Inventors: Kevin P. Campbell; Daniel Jung; Franck Duclos; Volker Straub, all of Iowa City, Iowa; John McPherson, St. Louis, Mo.

[73] Assignees: Washington University, St. Louis, Mo.; University of Iowa Research Foundation, Iowa City, Iowa

[21] Appl. No.: 719,758

[22] Filed: Sep. 25, 1996

[51] Int. Cl.$^6$ .......................... C12N 15/12; C12N 15/85; C12N 15/63

[52] U.S. Cl. ................ 435/325; 435/252.1; 435/320.1; 536/23.5

[58] Field of Search ................ 536/23.5; 935/9, 935/11; 435/69.1, 252.1, 325, 320.1

[56] References Cited

PUBLICATIONS

Nigro et al (1996) Human Molec. Genetics 5(8): 1179–1186.
Straub et al (1996) Amer. J. Hum. Genetics 59 (4, Suppl.): A286 (abstract #1660).
Duclos et al (1996) Amer. J. Hum. Genetics 59(4, Suppl): A38. (abstract #190).
Roberds et al., *Cell* 78: 625 (1994).
Noguchi et al., *Science* 270: 819 (1995).
Jung et al., *FEBS Lett.* 381: 15 (1996).
Passos–Bueno et al., *Hum. Mol. Genet.* 5: 815 (1996).
Bento Soares et al., *Proc. Natl. Acad. Sci. U.S.A.* 91: 9228 (1994).
Ohlendieck and Campbell, *J. Cell. Biol.* 115: 1685 (1991).
Ohlendieck et al., *J. Cell. Biol.* 112: 135 (1991).
Yamamoto et al., *J. Biochem.* 114: 132 (1993).

*Primary Examiner*—Paula K. Hutzell
*Assistant Examiner*—Robert C. Hayes
*Attorney, Agent, or Firm*—Kevin M. Farrell

[57] ABSTRACT

Disclosed herein is a substantially pure nucleic acid sequence encoding a mammalian 35 kDa non-dystrophin component (δ-sarcoglycan) of the dystrophin-glycoprotein complex. Also disclosed are the amino acid sequence and an immunogenic peptide of δ-sarcoglycan. The peptide when used to immunize a mammal, stimulates the production of antibodies which bind specifically to the δ-sarcoglycan. Methods to identify mutations in the δ-sarcoglycan gene associated with autosomal recessive limb-girdle muscular dystrophy are also disclosed. The identification of such mutations enables the design of nucleic acid probes which hybridize specifically to a mutant form of δ-sarcoglycan, or the complement thereof, but not to the DNA of the wild-type form of the gene (or the complement thereof), under stringent hybridization conditions. Such probes are useful, for example, in connection with the diagnosis of autosomal recessive limb-girdle muscular dystrophy. In addition, the identification of such mutations enables the diagnosis of autosomal recessive limb-girdle muscular dystrophy through the use of direct DNA sequencing techniques.

6 Claims, 1 Drawing Sheet

FIG. 1

SEQUENCE LISTING ( 1 ) GENERAL INFORMATION:

( i i i ) NUMBER OF SEQUENCES: 21

( 2 ) INFORMATION FOR SEQ ID NO:1:

( i ) SEQUENCE CHARACTERISTICS:
        ( A ) LENGTH: 1110 base pairs
        ( B ) TYPE: nucleic acid
        ( C ) STRANDEDNESS: single
        ( D ) TOPOLOGY: linear     ( i i ) MOLECULE TYPE: DNA (genomic)

( i x ) FEATURE:
        ( A ) NAME/KEY: CDS
        ( B ) LOCATION: 39..809

( x i ) SEQUENCE DESCRIPTION: SEQ ID NO:1:

```
TTACTGCCGG GAGTGTTGAG TGAAGGGACC AGGTGGAG ATG ATG CCT CAG GAG                   53
                                            Met Met Pro Gln Glu
                                             1               5

CAG TAC ACT CAC CAC CGG AGC ACC ATG CCT GGC TCT GTG GGG CCA CAG                101
Gln Tyr Thr His His Arg Ser Thr Met Pro Gly Ser Val Gly Pro Gln
                10                  15                  20

GTA TAC AAG GTG GGG ATT TAT GGC TGG CGG AAA CGA TGC CTG TAT TTC                149
Val Tyr Lys Val Gly Ile Tyr Gly Trp Arg Lys Arg Cys Leu Tyr Phe
            25                  30                  35

TTT GTC CTG CTC CTC ATG ATT TTA ATA CTG GTG AAC TTG GCC ATG ACC                197
Phe Val Leu Leu Leu Met Ile Leu Ile Leu Val Asn Leu Ala Met Thr
        40                  45                  50

ATC TGG ATT CTC AAA GTC ATG AAC TTC ACA ATT GAT GGA ATG GGA AAC                245
Ile Trp Ile Leu Lys Val Met Asn Phe Thr Ile Asp Gly Met Gly Asn
    55                  60                  65

CTG AGG ATC ACA GAA AAA GGT CTA AAG CTA GAA GGA GAC TCT GAA TTC                293
Leu Arg Ile Thr Glu Lys Gly Leu Lys Leu Glu Gly Asp Ser Glu Phe
70                  75                  80                  85

TTA CAA CCT CTC TAC GCC AAA GAA ATC CAG TCC CGA CCA GGT AAT GCC                341
Leu Gln Pro Leu Tyr Ala Lys Glu Ile Gln Ser Arg Pro Gly Asn Ala
                90                  95                 100

CTG TAC TTC AAG TCT GCC AGA AAT GTT ACA GTG AAC ATT CTC AAT GAC                389
Leu Tyr Phe Lys Ser Ala Arg Asn Val Thr Val Asn Ile Leu Asn Asp
           105                 110                 115

CAG ACT AAA GTG CTA ACT CAG CTT ATA ACA GGT CCA AAA GCC GTA GAA                437
Gln Thr Lys Val Leu Thr Gln Leu Ile Thr Gly Pro Lys Ala Val Glu
       120                 125                 130

GCT TAT GGT AAA AAA TTT GAG GTA AAA ACT GTT TCT GGA AAA TTG CTC                485
Ala Tyr Gly Lys Lys Phe Glu Val Lys Thr Val Ser Gly Lys Leu Leu
   135                 140                 145

TTC TCT GCA GAC AAT AAT GAA GTG GTA GTA GGA GCT GAA AGA TTA CGA                533
Phe Ser Ala Asp Asn Asn Glu Val Val Val Gly Ala Glu Arg Leu Arg
150                 155                 160                 165

GTT TTA GGA GCG GAG GGC ACA GTG TTC CCT AAA TCT ATA GAA ACA CCT                581
Val Leu Gly Ala Glu Gly Thr Val Phe Pro Lys Ser Ile Glu Thr Pro
                170                 175                 180

AAT GTC AGG GCA GAC CCC TTC AAA GAA CTA AGG TTG GAG TCC CCA ACC                629
Asn Val Arg Ala Asp Pro Phe Lys Glu Leu Arg Leu Glu Ser Pro Thr
           185                 190                 195
```

```
CGG  TCT  CTA  GTG  ATG  GAG  GCC  CCA  AAA  GGA  GTG  GAA  ATC  AAT  GCA  GAA    677
Arg  Ser  Leu  Val  Met  Glu  Ala  Pro  Lys  Gly  Val  Glu  Ile  Asn  Ala  Glu
          200                      205                     210

GCT  GGC  AAT  ATG  GAA  GCC  ACC  TGC  AGG  ACA  GAG  CTG  AGA  CTG  GAA  TCC    725
Ala  Gly  Asn  Met  Glu  Ala  Thr  Cys  Arg  Thr  Glu  Leu  Arg  Leu  Glu  Ser
          215                      220                     225

AAA  GAT  GGA  GAG  GTG  AGG  GAT  GAG  AAG  GAC  AGA  AGT  TCA  AAG  AGC  TAC    773
Lys  Asp  Gly  Glu  Val  Arg  Asp  Glu  Lys  Asp  Arg  Ser  Ser  Lys  Ser  Tyr
230                      235                     240                     245

AGC  TTC  AAC  AGG  CCA  ACC  CTT  CCC  ATA  ACT  GGT       TGACCTCGGA  GTTGGATCCT    826
Ser  Phe  Asn  Arg  Pro  Thr  Leu  Pro  Ile  Thr  Gly
                    250                     255

ACAGTGTATC  AACAAAAGGA  GCCAAGCAGG  TTTTATTTCT  GAAACAATTA  ATTGAGCAGC    886

ATGATTATAA  GCCAAACCCA  CAATCCATCA  AAGTGATGAT  TTCTTATTTG  TAAAATGCGG    946

AGATAATGGC  ATGTATTCCA  AGTACAGAAT  TATATGACCA  TGAAAATGAA  TGCTATTTTC   1006

AAATTCTCTC  TTGTCACCTT  AAAATAAGAT  TTTGTTAGCC  AACATAATTA  AGCTGTATAT   1066

ATTATACACA  TCTGGCTCAA  GAAAAAAAAA  AAAAAAAAAA  AAAA                    1110
```

( 2 ) INFORMATION FOR SEQ ID NO:2:

( i ) SEQUENCE CHARACTERISTICS:
        ( A ) LENGTH: 256 amino acids
        ( B ) TYPE: amino acid
        ( D ) TOPOLOGY: linear     ( i i ) MOLECULE TYPE: protein     ( x i ) SEQUENCE DESCRIPTION: SEQ ID NO:2:

```
Met  Met  Pro  Gln  Glu  Gln  Tyr  Thr  His  His  Arg  Ser  Thr  Met  Pro  Gly
1                   5                        10                      15

Ser  Val  Gly  Pro  Gln  Val  Tyr  Lys  Val  Gly  Ile  Tyr  Gly  Trp  Arg  Lys
               20                       25                      30

Arg  Cys  Leu  Tyr  Phe  Phe  Val  Leu  Leu  Leu  Met  Ile  Leu  Ile  Leu  Val
                    35                       40                      45

Asn  Leu  Ala  Met  Thr  Ile  Trp  Ile  Leu  Lys  Val  Met  Asn  Phe  Thr  Ile
          50                       55                      60

Asp  Gly  Met  Gly  Asn  Leu  Arg  Ile  Thr  Glu  Lys  Gly  Leu  Lys  Leu  Glu
65                       70                       75                          80

Gly  Asp  Ser  Glu  Phe  Leu  Gln  Pro  Leu  Tyr  Ala  Lys  Glu  Ile  Gln  Ser
                         85                       90                      95

Arg  Pro  Gly  Asn  Ala  Leu  Tyr  Phe  Lys  Ser  Ala  Arg  Asn  Val  Thr  Val
               100                      105                     110

Asn  Ile  Leu  Asn  Asp  Gln  Thr  Lys  Val  Leu  Thr  Gln  Leu  Ile  Thr  Gly
               115                      120                     125

Pro  Lys  Ala  Val  Glu  Ala  Tyr  Gly  Lys  Lys  Phe  Glu  Val  Lys  Thr  Val
     130                      135                     140

Ser  Gly  Lys  Leu  Leu  Phe  Ser  Ala  Asp  Asn  Glu  Val  Val  Val  Gly
145                      150                     155                     160

Ala  Glu  Arg  Leu  Arg  Val  Leu  Gly  Ala  Glu  Gly  Thr  Val  Phe  Pro  Lys
                    165                      170                     175

Ser  Ile  Glu  Thr  Pro  Asn  Val  Arg  Ala  Asp  Pro  Phe  Lys  Glu  Leu  Arg
               180                      185                     190

Leu  Glu  Ser  Pro  Thr  Arg  Ser  Leu  Val  Met  Glu  Ala  Pro  Lys  Gly  Val
          195                      200                     205

Glu  Ile  Asn  Ala  Glu  Ala  Gly  Asn  Met  Glu  Ala  Thr  Cys  Arg  Thr  Glu
     210                      215                     220
```

```
        Leu  Arg  Leu  Glu  Ser  Lys  Asp  Gly  Glu  Val  Arg  Asp  Glu  Lys  Asp  Arg
        225                      230                     235                     240

Ser  Ser  Lys  Ser  Tyr  Ser  Phe  Asn  Arg  Pro  Thr  Leu  Pro  Ile  Thr  Gly
                           245                     250                     255
```

( 2 ) INFORMATION FOR SEQ ID NO:3:

( i ) SEQUENCE CHARACTERISTICS:
        ( A ) LENGTH: 11 amino acids
        ( B ) TYPE: amino acid
        ( C ) STRANDEDNESS: single
        ( D ) TOPOLOGY: linear     ( i i ) MOLECULE TYPE: peptide     ( x i ) SEQUENCE DESCRIPTION: SEQ ID NO:3:

```
        Val  Leu  Gly  Ala  Glu  Gly  Thr  Val  Phe  Pro  Lys
        1                   5                        10
```

( 2 ) INFORMATION FOR SEQ ID NO:4:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear     ( i i ) MOLECULE TYPE: peptide     ( x i ) SEQUENCE DESCRIPTION: SEQ ID NO:4:

```
        Glu  Gln  Tyr  Leu  Thr  Ala  Thr  Glu
        1                   5
```

( 2 ) INFORMATION FOR SEQ ID NO:5:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear     ( i i ) MOLECULE TYPE: peptide     ( x i ) SEQUENCE DESCRIPTION: SEQ ID NO:5:

```
        Asp  Gly  Leu  Ile  Leu  Glu  Gly  Glu  Ser
        1                   5
```

( 2 ) INFORMATION FOR SEQ ID NO:6:

( i ) SEQUENCE CHARACTERISTICS:
        ( A ) LENGTH: 19 amino acids
        ( B ) TYPE: amino acid
        ( C ) STRANDEDNESS: single
        ( D ) TOPOLOGY: linear     ( i i ) MOLECULE TYPE: peptide     ( x i ) SEQUENCE DESCRIPTION: SEQ ID NO:6:

```
        Leu  Lys  Val  Gly  Pro  Gln  Xaa  Val  Glu  Val  Gln  Ser  Gln  Gln  Xaa  Gln
        1                   5                        10                      15

Ile  Asn  Ser
```

( 2 ) INFORMATION FOR SEQ ID NO:7:

( i ) SEQUENCE CHARACTERISTICS:
        ( A ) LENGTH: 17 amino acids
        ( B ) TYPE: amino acid
        ( C ) STRANDEDNESS: single (D) TOPOLOGY: linear (ii) MOLECULE TYPE: peptide (xi) SEQUENCE DESCRIPTION: SEQ ID NO:7:

```
Ser Leu Phe Thr Val Asp Glu Glu Glu Val Val Val Gly Thr Asp Arg
1               5                   10                  15
Leu
```

(2) INFORMATION FOR SEQ ID NO:8:

(i) SEQUENCE CHARACTERISTICS:
        (A) LENGTH: 18 amino acids
        (B) TYPE: amino acid
        (C) STRANDEDNESS: single
        (D) TOPOLOGY: linear     (ii) MOLECULE TYPE: peptide     (xi) SEQUENCE DESCRIPTION: SEQ ID NO:8:

```
Val Thr Gly Pro Glu Gly Ala Leu Phe Glu His Ser Val Glu Thr Pro
1               5                   10                  15
Leu Val
```

(2) INFORMATION FOR SEQ ID NO:9:

(i) SEQUENCE CHARACTERISTICS:
        (A) LENGTH: 7 amino acids
        (B) TYPE: amino acid
        (C) STRANDEDNESS: single
        (D) TOPOLOGY: linear     (ii) MOLECULE TYPE: peptide     (xi) SEQUENCE DESCRIPTION: SEQ ID NO:9:

```
Ser Leu Ser Met Asp Ala Pro
1               5
```

(2) INFORMATION FOR SEQ ID NO:10:

(i) SEQUENCE CHARACTERISTICS:
        (A) LENGTH: 10 amino acids
        (B) TYPE: amino acid
        (C) STRANDEDNESS: single
        (D) TOPOLOGY: linear     (ii) MOLECULE TYPE: peptide     (xi) SEQUENCE DESCRIPTION: SEQ ID NO:10:

```
Leu Val Gln Gly Thr Gln Ala Ala Ser Gly
1               5                   10
```

(2) INFORMATION FOR SEQ ID NO:11:

(i) SEQUENCE CHARACTERISTICS:
        (A) LENGTH: 13 amino acids
        (B) TYPE: amino acid
        (C) STRANDEDNESS: single
        (D) TOPOLOGY: linear     (ii) MOLECULE TYPE: peptide     (xi) SEQUENCE DESCRIPTION: SEQ ID NO:11:

```
Ser Thr Met Pro Gly Ser Val Gly Pro Gln Val Tyr Lys
1               5                   10
```

(2) INFORMATION FOR SEQ ID NO:12:

( i ) SEQUENCE CHARACTERISTICS:
   ( A ) LENGTH: 17 amino acids
   ( B ) TYPE: amino acid
   ( C ) STRANDEDNESS: single
   ( D ) TOPOLOGY: linear ( i i ) MOLECULE TYPE: peptide ( x i ) SEQUENCE DESCRIPTION: SEQ ID NO:12:

Gly Leu Lys Leu Glu Gly Asp Ser Glu Phe Leu Gln Pro Leu Tyr Ala
1               5                   10                  15

Lys ( 2 ) INFORMATION FOR SEQ ID NO:13:

( i ) SEQUENCE CHARACTERISTICS:
      ( A ) LENGTH: 13 amino acids
      ( B ) TYPE: amino acid
      ( C ) STRANDEDNESS: single
      ( D ) TOPOLOGY: linear ( i i ) MOLECULE TYPE: peptide ( x i ) SEQUENCE DESCRIPTION: SEQ ID NO:13:

Glu Ile Gln Ser Arg Pro Gly Asn Ala Leu Tyr Phe Lys
1               5                   10

( 2 ) INFORMATION FOR SEQ ID NO:14:

( i ) SEQUENCE CHARACTERISTICS:
      ( A ) LENGTH: 11 amino acids
      ( B ) TYPE: amino acid
      ( C ) STRANDEDNESS: single
      ( D ) TOPOLOGY: linear ( i i ) MOLECULE TYPE: peptide ( x i ) SEQUENCE DESCRIPTION: SEQ ID NO:14:

Asn Val Thr Val Asn Ile Leu Asp Gln Thr Lys
1               5                   10

( 2 ) INFORMATION FOR SEQ ID NO:15:

( i ) SEQUENCE CHARACTERISTICS:
      ( A ) LENGTH: 9 amino acids
      ( B ) TYPE: amino acid
      ( C ) STRANDEDNESS: single
      ( D ) TOPOLOGY: linear ( i i ) MOLECULE TYPE: peptide ( x i ) SEQUENCE DESCRIPTION: SEQ ID NO:15:

Val Leu Thr Gln Leu Ile Thr Gly Pro
1               5

( 2 ) INFORMATION FOR SEQ ID NO:16:

( i ) SEQUENCE CHARACTERISTICS:
      ( A ) LENGTH: 5 amino acids
      ( B ) TYPE: amino acid
      ( C ) STRANDEDNESS: single
      ( D ) TOPOLOGY: linear ( i i ) MOLECULE TYPE: peptide ( x i ) SEQUENCE DESCRIPTION: SEQ ID NO:16:

Lys Phe Glu Val Lys
1               5

( 2 ) INFORMATION FOR SEQ ID NO:17:

( i ) SEQUENCE CHARACTERISTICS:
        ( A ) LENGTH: 15 amino acids
        ( B ) TYPE: amino acid
        ( C ) STRANDEDNESS: single
        ( D ) TOPOLOGY: linear     ( i i ) MOLECULE TYPE: peptide     ( x i ) SEQUENCE DESCRIPTION: SEQ ID NO:17:

```
Leu Phe Ser Ala Asp Met Asn Asn Xaa Val Val Gly Ala Phe Arg
1               5                   10                  15
```

( 2 ) INFORMATION FOR SEQ ID NO:18:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear     ( i i ) MOLECULE TYPE: peptide     ( x i ) SEQUENCE DESCRIPTION: SEQ ID NO:18:

```
Ile Glu Thr Pro Asn Val Arg
1               5
```

( 2 ) INFORMATION FOR SEQ ID NO:19:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear     ( i i ) MOLECULE TYPE: peptide     ( x i ) SEQUENCE DESCRIPTION: SEQ ID NO:19:

```
Ala Asp Pro Phe Lys Glu Leu
1               5
```

( 2 ) INFORMATION FOR SEQ ID NO:20:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear     ( i i ) MOLECULE TYPE: peptide     ( x i ) SEQUENCE DESCRIPTION: SEQ ID NO:20:

```
Ser Leu Val Met Glu Ala Pro
1               5
```

( 2 ) INFORMATION FOR SEQ ID NO:21:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear     ( i i ) MOLECULE TYPE: peptide     ( x i ) SEQUENCE DESCRIPTION: SEQ ID NO:21:

```
Val Glu Ile Asn Ala Glu Ala Gly Asn Met Glu Ala
1               5                   10
```

δ-SARCOGLYCAN NUCLEIC ACID SEQUENCES

BACKGROUND OF THE INVENTION

The dystrophin-glycoprotein complex (DGC) in skeletal muscle is a complex of sarcolemmal proteins and glycoproteins. It is composed of dystrophin, a cytoskeletal actin-binding protein; the syntrophins, a 59 kDa triplet of intracellular proteins that bind the C-terminal domain of dystrophin; α-dystroglycan, a 156 kDa extracellular proteoglycan which binds the G domain of laminin; β-dystroglycan, a 43 kDa transmembrane glycoprotein which binds the cysteine-rich region of dystrophin, α-, β-, and γ-sarcoglycan, transmembrane glycoproteins of 50, 43, and 35 kDa respectively; and a 25 kDa transmembrane protein. Recent experiments have demonstrated the existence of two complexes within the DGC: the dystroglycan complex, composed of α- and β-dystroglycan, and the sarcoglycan complex, consisting of α-, β-, and γ-sarcoglycan.

Defects in DGC components lead to muscle fiber necrosis, the major pathological event in muscular dystrophies. In Duchenne muscular dystrophy (DMD), mutations in the dystrophin gene cause the loss of dystrophin and a reduction of the dystrophin-associated proteins. One form of congenital muscular dystrophy (CMD) has recently been characterized as being caused by mutations in the laminin α2-chain gene. Limb-girdle muscular dystrophy (LGMD) represents a clinically and genetically heterogeneous class of disorders. They are inherited as either autosomal dominant or recessive traits. An autosomal dominant form, LGMD1A, was mapped to 5q31–q33 (Speer, M. C. et al., *Am. J. Hum. Genet.* 50:1211, 1992; Yamaoka, L. Y. et al., *Neuromusc. Disord.* 4:471, 1994), while six genes involved in the autosomal recessive forms were mapped to 15q15.1 (LGMD2A)(Beckmann, J. S. et al., *C. R. Acad. Sci. Paris* 312:141, 1991), 2p16-p13 (LGMD2B)(Bashir, R. et al., *Hum. Mol. Genet.* 3:455, 1994), 13q12 (LGMD2C)(Ben Othmane, K. et al., *Nature Genet.* 2:315, 1992; Azibi, K. et al., *Hum. Mol. Genet.* 2:1423, 1993), 17q12–q21.33 (LGMD2D)(Roberds, S. L. et al., *Cell* 78:625, 1994; McNally, E. M., et. al., *Proc. Nat. Acad. Sci. U. S. A.* 91:9690, 1994), 4q12 (LG1MD2E)(Lim, L. E., et. al., *Nat. Genet.* 11:257, 1994; Bönnemann, C. G. et al. *Nat. Genet.* 11:266, 1995), and most recently to 5q33–q34 (LGMD2F) (Passos-Bueno, M. R., et. al., *Hum. Mol. Genet.* 5:815, 1996). Patients with LGMD2C, 2D and 2E have a deficiency of components of the sarcoglycan complex resulting from mutations in the genes encoding γ-, α-, and β-sarcoglycan respectively. The gene responsible for LGMD2A has been identified as the muscle-specific calpain, whereas the genes responsible for LGMD1A, 2B and 2F are still unknown.

SUMMARY OF THE INVENTION

In one aspect, the present invention relates to a substantially pure nucleic acid sequence encoding a mammalian 35 kDa non-dystrophin component (δ-sarcoglycan) of the dystrophin-glycoprotein complex. The substantially pure nucleic acid sequence is characterized by the ability to hybridize to the DNA sequence of SEQ ID NO:1, or the complement thereof, under stringent hybridization conditions. The substantially pure nucleic acid molecule of the present invention can also be characterized as encoding the amino acid sequence shown in SEQ ID NO:2, or equivalents of said amino acid sequence. The invention also encompasses DNA expression constructs incorporating the substantially pure nucleic acid sequence encoding δ-sarcoglycan, and cells (prokaryotic and eukaryotic) which harbor such an expression construct. Such compositions are useful, for example, in the production of highly pure immunogen for use in stimulating the production of polyclonal and monoclonal antibodies.

In another aspect, the present invention relates to immunogenic peptides (or equivalents thereof) which, when used to immunize a mammal, stimulate the production of antibodies which bind specifically to the δ-sarcoglycan. Such peptides are useful, for example, in the production of highly pure immunogen for use in stimulating the production of polyclonal and monoclonal antibodies.

Another aspect of the present invention relates to direct sequencing methods for the determination of mutations responsible for disorders such as autosomal recessive limb-girdle muscular dystrophy. Based on the information obtained through direct sequencing, nucleic acid probes can be designed which hybridize specifically to a mutant form of δ-sarcoglycan, or the complement thereof, but not to the DNA of the wild-type form of the gene (or the complement thereof), under stringent hybridization conditions. Such probes are useful, for example, in connection with the diagnosis of autosomal recessive limb-girdle muscular dystrophy.

BRIEF DESCRIPTION OF THE DRAWINGS

FIG. 1 is a diagrammatic representation which shows the chromosomal localization of the δ-sarcoglycan gene. The radiation hybrid map generated for this study (center) is shown aligned with the relevant portions of the December 1995 release of the whole genome maps from the Whitehead Institute (WI). The region linked to LGMD2F in family LG26 the minimal interval for LGMD2F are indicated by the vertical lines on the right. The positioning of δ-sarcoglycan is described in detail below. Selected markers which are on multiple maps are connected with black lines.

DETAILED DESCRIPTION OF THE INVENTION

The present invention is based, in one aspect, on the isolation of a cDNA sequence encoding a mammalian 35 kDa non-dystrophin component of the dystrophin-glycoprotein complex. This component is referred to herein as δ-sarcoglycan. The isolated cDNA of the present invention can be used in a variety of contexts. For example, the sequence information disclosed herein can be used to isolate nucleic acids, other than cDNA, which encode δ-sarcoglycan. Such nucleic acids include, for example, intron-containing genomic DNA sequences. In addition, any complementary nucleic acid (both DNA and RNA) that will form a duplex structure with the δ-sarcoglycan sequence disclosed herein can be included.

The isolated cDNA sequence of the present invention can be inserted in an expression vector. Such vectors contain all necessary regulatory signals to promote the expression of a DNA sequence of interest. Expression vectors are typically either prokaryote specific, or eukaryote specific. However, vectors have been developed which can promote the expression of a DNA sequence of interest in either a prokaryotic or eukaryotic system. Such vectors are known as shuttle vectors.

Prokaryotic expression vectors are useful for the preparation of large quantities (e.g., up to milligram quantities) of the protein encoded by the DNA sequence of interest. Eukaryotic expression vectors are useful when the addition of carbohydrate side chains, (i.e. glycosylation) to the protein is important. The carbohydrate sidechains can affect the properties of a protein in a variety of ways including, for example, the ability of the protein to function in vivo or in vitro; the ability of the protein to form a complex and associate with other proteins or nucleic acids; and ability of the protein to bind to an antibody or other molecule specific for the protein of interest.

Following purification by conventional methods, recombinantly produced δ-sarcoglycan, or an immunogenic portion of same, can be used as a source of highly purified immunogen for the generation of antibodies. Alternatively, a crude lysate can be used in many circumstances. As disclosed in U.S. Pat. No. 5,308,752, the disclosure of which is incorporated herein by reference, levels of δ-sarcoglycan are greatly reduced in an animal model for Duchenne muscular dystrophy. Thus, antibodies reactive with δ-sarcoglycan, produced as described herein, are useful in connection with diagnosis of muscular dystrophy by the detection of δ-sarcoglycan levels within the cells of a tissue.

Polyclonal antibodies can be prepared by immunizing an animal with immunogen prepared as described above using conventional techniques (see e.g., Harlow and Lane (Eds.), *Antibodies, A Laboratory Manual* (Cold Spring Harbor Laboratory, Cold Spring Harbor, N.Y. (1988)). Briefly, the immunized animal is maintained under conditions whereby antibodies reactive with the immunogen are produced. Blood is collected from the animal upon reaching a desired antibody titer. The serum containing the polyclonal antibodies is separated from the other blood components. The polyclonal antibody-containing serum can optionally be further separated into fractions of particular types of antibodies (e.g., IgG or IgM) or monospecific antibodies can be purified from polyclonal antibody containing serum.

Similarly, polyclonal antibody secreting hybridomas can be produced using conventional techniques (see e.g., Harlow and Lane (Eds.), *Antibodies, A Laboratory Manual* (Cold Spring Harbor Laboratory, Cold Spring Harbor, N.Y. (1988)). In a preferred embodiment, anti-δ-sarcoglycan monoclonal antibodies are produced by murine hybridomas formed by fusion of: a) a mouse myeloma or hybridoma which does not secrete antibody with b) murine spleen cells which secrete antibodies obtained from mice immunized against δ-sarcoglycan as described in the preceding paragraph.

Typically, the mice are immunized with a primary injection of δ-sarcoglycan followed by a number of boosting injections of the immunogen. During or after the immunization procedure, sera of the mice is screened to identify those mice in which a substantial immune response has been evoked. For selected mice, the spleen cells are obtained and fusions are performed. Suitable fusion techniques are the Sendai virus technique (Kohler and Milstein, *Nature* 256: 495 (1975)), or the polyethylene glycol method (Kennet, "*Monoclonal Antibodies, Hybridomas - A New Dimension in Biological Analysis*", Eds. Kennet, McKern and Bechtol, Plenum Press, NY (1980)).

The hybridomas are then screened for production of antibodies specific for δ-sarcoglycan. A suitable screening technique is a solid phase radioimmunoassay. A solid phase is prepared by coupling δ-sarcoglycan to an insoluble matrix. The immunoadsorbent is brought into contact with culture supernatants of hybridomas. After a period of incubation, the solid phase is separated from the supernatants, then contacted with a labeled antibody against murine immunoglobulin. Label associated with the immunoadsorbent indicates the presence of hybridoma products reactive with δ-sarcoglycan.

The monoclonal antibodies can be produced in large quantities by injecting anti-δ-sarcoglycan antibody producing cells into the peritoneal cavity of mice and, after an appropriate time, harvesting ascites fluid from the mice which yield a high titer of homogenous antibody. The monoclonal antibodies are then isolated from the fluid. Alternatively, the antibodies can be produced by culturing anti-δ-sarcoglycan antibodies producing cells in vitro and isolating secreted monoclonal antibodies from the culture medium directly.

The Exemplification section which follows describes experiments in which a single immunogenic peptide was used to immunize animals resulting in the production of antibodies which bind specifically to δ-sarcoglycan. More specifically, the peptide specified in SEQ ID NO:3 was demonstrated to stimulate an immune response. Thus, in another aspect, the present invention relates to immunogenic peptides capable of stimulating such a response, or equivalents of such peptides. Equivalents, as used in this context, includes peptides of substantially similar length and amino acid identity to those disclosed but having a conservative amino acid substitution at a non-critical residue. A conservative amino acid substitution is a substitution in which an amino acid residue is replaced with an amino acid residue of differing identity, but whose R group can be characterized as chemically similar. Four common categories which are defined in standard biochemical texts include: polar but uncharged R groups; positively charged R groups; negatively charged R groups; and hydrophobic R groups. A preferred conservative substitution involves the substitution of a second hydrophobic residue for a first hydrophobic residue, the first and second hydrophobic residues differing primarily in the size of the R group. The hydrophobic reside would be predicted to be located internally in the folded peptide structure and the mild perturbation caused only by a change in the size of an R group at an internal location in the folded peptide structure would not be predicted to alter the antigenic properties of the peptide.

The present invention encompasses not only the nucleic acid sequence disclosed in SEQ ID NO: 1, and fragments thereof, but also related DNA sequences which hybridize to the DNA of SEQ ID NO: 1, or the complement thereof under stringent hybridization conditions. Such related DNA sequences would include, for example, DNA encoding isoforms produced through alternative splicing. A nucleic acid sequence would fall within the scope of the invention, for example, under the following circumstances. The DNA molecule represented in SEQ ID NO: 1 is fixed to a solid support and a second DNA molecule to be tested for the ability to hybridize to the DNA of SEQ ID NO: 1 is detectably labeled and suspended in a hybridization buffer consisting essentially of 50% formamide, 5 X SSPE (1 X SSPE is 0.15 mM NaCl, 1 mM Na-EDTA, 10 mM Na-phosphate (pH 7.0), 5 X Denhardt's solution (0.1% polyvinylpyrrolidone, 0.1% Ficoll)). The hybridization buffer is contacted with the solid support at a temperature of about 45° C. for a period of several hours. The hybridization solution is then removed, and non-specifically bound nucleic acid is removed by repeated washing with 1 X SSC at increasing temperatures (up to 65° C.).

The substantially pure nucleic acid molecule of the present invention can also be characterized as encoding the amino acid sequence shown in SEQ ID NO:2, or equivalents of said amino acid sequence. Equivalents, as used in this context, includes sequences of substantially amino acid identity to those disclosed but having a conservative amino acid substitution at a non-critical residue. A conservative amino acid substitution is a substitution in which an amino acid residue is replaced with an amino acid residue of differing identity, but whose R group can be characterized as chemically similar. As discussed previously, four common categories which are defined in standard biochemical texts include: polar but uncharged R groups; positively charged R groups; negatively charged R groups; and hydrophobic R groups. A preferred conservative substitution involves the substitution of a second hydrophobic residue for a first hydrophobic residue, the first and second hydrophobic residues differing primarily in the size of the R group. The hydrophobic reside would be predicted to be located internally in the folded peptide structure and the mild perturbation caused only by a change in the size of an R group at an internal location in the folded peptide structure would not be predicted to alter the antigenic properties of the peptide.

In another aspect, the present invention relates to diagnostic screening techniques useful for the identification of mutations within the δ-sarcoglycan gene which are responsible for certain myopathies such as autosomal recessive limb-girdle muscular dystrophy. Initial identification of mutations responsible for such conditions can be made, for example, by producing cDNA from the mRNA of an individual suffering from limb-girdle muscular dystrophy, or from an individual whose family history indicates a predisposition to the indicated syndrome. The sequence of nucleotides in the cDNA is then determined by conventional techniques. This determined sequence is then compared to the wild-type sequence disclosed in SEQ ID NO: 1. Differences between the determined cDNA sequence, and that disclosed in SEQ ID NO: 1 are candidate deleterious mutations.

To determine whether such mutations are responsible, for example, for autosomal recessive limb-girdle muscular dystrophy, experiments could be designed in which the defective gene carrying the identified mutation is introduced into an otherwise normal cellular background wherein the gene encoding wild-type δ-sarcoglycan has been deleted or otherwise inactivated. The ability of the mutant δ-sarcoglycan to participate in the assembly of the sarcoglycan complex can be assessed using conventional techniques such as those described in the Exemplification section which follows.

By conducting experiments of this type, a variety of mutations can be identified which affect the assembly of the sarcoglycan complex. Improper assembly of this complex is known to be associated with limb-girdle muscular dystrophy. Thus, given the identification of such mutations it is possible to design nucleic acid probes useful for the detection of such mutations within a DNA molecule. The use of such probes for the identification of a specific mutation in a DNA molecule is much simpler than the determination of the entire sequence, followed by comparison to wild-type. In preferred embodiments, such probes have a length of between about 20–30 nucleotides, with a single mismatch relative to the wild-type sequence.

Another aspect of the present invention includes the complementation of a defective mutant gene (e.g., identified as describe above) in an affected individual by the introduction of a genetic construct carrying DNA encoding functional δ-sarcoglycan. The introduction of such a complementary copy of the δ-sarcoglycan gene can be accomplished through the use of any of the conventional techniques which are known to be effective.

EXEMPLIFICATION

I. Experimental Procedures

Peptide Sequencing and Isolation of Human δ-Sarcoglycan cDNA.

Peptides of the 35 kDa component of purified rabbit skeletal muscle DGC were obtained as previously described (Jung, D. et al. *FEBS Lett.* 381:15, 1996). These peptide sequences were used to search the database of expressed sequence tags (dbEST) using the TBLASTN search program at the National Center for Biotechnology Information. An EST isolated from human placenta cDNA library was identified. Clone 259220, from which EST was generated, was obtained from Research Genetics, Inc. The clone was fully sequenced on both strands using an Applied Biosystems, Inc. automated sequencer and determined to contain the full coding region of the human δ-sarcoglycan cDNA. Primary structure and site detection analysis were performed using PC/GENE software (Oxford Molecular).

Northern Blot Analysis.

CLONTECH adult human multiple tissue northern blots containing 2 μg of poly(A)+RNA per lane were probed with the full length δ-sarcoglycan cDNA clone.

Antibodies to Components of the Dystrophin Glycoprotein Complex.

Antibodies against the different components of the dystrophin-glycoprotein complex were produced in a goat using the purified rabbit skeletal muscle dystrophin-glycoprotein complex (Campbell, K. P. & Kahl, S. D., *Nature* 338:259, 1989) as previously performed with a sheep (Ohlendieck, K., and Campbell, K. P., *J. Cell. Biol.* 115:1685, 1991) (Elmira Biologicals). Goat 20 antiserum recognizes all components of the DGC and specific antibodies were affinity purified using immobilon P strips of DGC components or fusion proteins of DGC components. Monoclonal antibodies VIA42 against dystrophin, and IVD31 against α-sarcoglycan were previously characterized (Ervasti, J. M., et. al., *Nature* 345:315, 1990). Affinity-purified rabbit #172 antibody against β-sarcoglycan and affinity-purified sheep #0025 antibody against γ-sarcoglycan were previously characterized (Lim, L. E., et. al. *Nat. Genet.* 11:257, 1995; Jung, D. et al. *FEBS Lett.* 381:1521, 1996). Monoclonal antibody against human laminin (MAB1922) α2 chain was purchased from Chemicon.

δ-Sarcoglycan Antibodies.

A peptide corresponding to the rabbit skeletal muscle δ-sarcoglycan sequence amino acids 166 to 176, was chemically synthesized with an additional cysteine at the N-terminus. This synthetic peptide was conjugated with the N-terminal cysteine of keyhole limpet hemocyanin (Pierce Chemical Co.) using m-maleimidobenzoic acid-N-hydroxysuccinimide ester (Pierce Chemical Co.), mixed with Freund's adjuvant (Sigma Chemical Co.) and injected into sheep #0074. Polyclonal antibodies against the peptide were affinity purified from crude sera using BSA-conjugated peptide as previously described (Lim, L. E., et. al., *Nat. Genet.* 11:257, 1995).

Fusion Protein Constructs.

The extracellular domains of γ-sarcoglycan (amino acids 62–291) and δ-sarcoglycan (amino acids 93–256) were amplified by PCR in a Perkin Elmer Thermocycler using specific primers containing BamHI or EcoRI restriction sites. Following restriction digest with BamHI and EcoRI, the products were subcloned into pGEX2TK (Smith, D. B. and Johnson, K. S., *Gene* 67:31, 1988) and introduced into DH5α cells. Overnight cultures (50 ml) were diluted 1:10 and induced with IPTG (United States Biochemicals) to promote fusion protein production. Fusion proteins were purified on a glutathione-agarose column.

Immunoblot and Immunofluorescence Analysis.

Crude rabbit skeletal muscle sarcolemma, purified DGC (Ervasti, J. M., et. al., *J. Biol. Chem.* 266:9161, 1991), and isolated sarcoglycan complex (Ohlendieck, K., et. al., *J. Cell. Biol.* 112:135, 1991) were prepared as previously described. Proteins were resolved on a 3%–12%, 3%–20%, 5%–12% or 10% SDS polyacrylamide gel, stained with Coomassie blue or transferred to nitrocellulose by electroblotting. Blots were incubated overnight in a 1:15 dilution of affinity-purified anti-δ-sarcoglycan antibody, 1:15 dilution of affinity-purified anti-γ-sarcoglycan antibody or 1:15 dilution of affinity-purified anti-Fusion protein M from goat 20 antibody in Blotto (5% nonfat dried milk in TBS [20 mM Tris-HCl, 200 mM NaCl, pH 7.4]). Blots were then incubated with a horseradish peroxidase-conjugated anti-sheep IgG or anti-goat IgG secondary antibody (Boehringer Mannheim) for 1 hr. Antibody staining was detected with $H_2O_2$ in TBS with 4-chloro-1-naphthol as a substrate or by ECL (Amersham). Coomassie Blue stained gels were analyzed densitometrically using a Molecular Dynamics Model 300A scanning densitometer.

For immunofluorescence, 7 μm transverse cryosections were prepared from control, DMD and LGMD muscle biopsies. The following procedures were performed at room temperature. Sections were treated with AB blocking solutions (Vector), blocked with 5% BSA in PBS for 30 min., and then incubated with a 1:20 dilution of affinity-purified anti-δ-sarcoglycan antibody in 5% BSA/PBS for 90 min. Antibodies against the following components of the DGC were also tested: dystrophin, laminin α2 chain, α-sarcoglycan, β-sarcoglycan, and γ-sarcoglycan. After extensive washing with PBS/1% BSA, sections were incubated with biotinylated secondary antibodies (1:500) for 30 min., washed with PBS/1% BSA, and then incubated with FITC-conjugated streptavidin (1:1000) for 30 min. After rinsing with PBS, sections were mounted with FITC-guard (Testog) and observed under a Zeiss Axioplan fluorescence microscope.

Enzymatic Deglycosylation.

DGC (0.5 mg/ml) in 20 mM $NaHPO_4$ pH 7.5, 50 mM EDTA and 0.2% SDS was boiled for 2 min and incubated 16 hr at 37° C. after addition of 1% Triton X100 and 5U of endoglycosidase/PNGaseF (Oxford Glycosystems). After incubation the samples were resolved on 10% or 5%–15% SDS-PAGE and analyzed either on Western blot with the affinity-purified anti-δ-sarcoglycan and affinity-purified anti-γ-sarcoglycan antibodies or by Coomassie blue staining.

Localization of the δ-Sarcoglycan Gene to Chromosome 5q33–q34.

Primers corresponding to human δ-sarcoglycan cDNA nucleotides 781–800 (sense) and 1040–1060 (anti-sense) were used to amplify a 280 bp product. The following cycling parameters were used: 94° C., 3 min; (94° C.,:30 min 58° C.,:30 min 72° C.,:30 min)×35; 72° C., 7 min. DNA from a panel of 25 human rodent somatic cell hybrids (BIOS Corporation) containing various combinations of human chromosomes or different region of chromosome 5q and DNA isolated from 180 chromosome 5-specific radiation hybrids were analyzed by PCR. PCR products were separated using 3% agarose and the hybrids scored for the presence or absence of the specific PCR product using ethidium bromide. The position of the δ-sarcoglycan locus relative to previously analyzed markers was determined using the rh2pt and rhmaxlik programs (Boehnke M., et. al., *Am. J. Hum. Genet.* 49:1174, 1991).

II. Results

δ-Sarcoglycan cDNA and Primary Structure Analysis

To characterize the 35 kDa component of the DGC, purified rabbit skeletal muscle DGC was separated by SDS-PAGE and transferred to PVDF membrane. The region of the membrane containing the 35 kDa protein was excised and the immobilized protein was digested with trypsin. Peptides were purified by reverse-phase HPLC and subjected to amino acid sequencing by Edman degradation. Different peptide sequences were obtained (Table 1). These peptide sequence fragments were compared with the protein sequence of the recently reported γ-sarcoglycan primary structure, a 35 kDa component of the DGC. Several of these peptide sequences were not found in the reported γ-sarcoglycan sequence, indicating the existence of at least a second protein of similar molecular weight within the DGC.

To characterize this second 35 kDa protein, the GenBank database of expressed sequence tags (dbEST) was searched with the unidentified peptide sequences. An EST encoding one of the peptide fragments was identified and isolated from a normalized human placenta cDNA library constructed by Dr. Bento Soares et al. (Bento Soares, M. et al., *Proc. Natl. Acad. Sci. U.S.A.* 91:9228, 1994). Clone 259220, from which the EST was generated, was obtained from the IMAGE Consortium and fully sequenced on both strands. The 1.1 kb cDNA sequence contains a single 768 bp open reading frame with a presumptive initiator methionine at nucleotide 38 preceded by an in-frame stop codon, a stop codon at nucleotide 806, and a poly(A)+tail. The open reading frame encodes a protein of 256 amino acids with a predicted molecular weight of 29 kDa, a predicted isoelectric point of 9.48 and contains most of the 35 kDa peptides that were not present in the primary structure of γ-sarcoglycan (Table 1, SEQ ID NO:1). Amino acid sequence analysis revealed a single transmembrane domain and no N-terminal signal sequence. Therefore, the protein is likely to be a type II transmembrane protein with an intracellular N-terminus. This membrane topology is consistent with the location of two putative N-linked glycosylation sites, which are C-terminal to the transmembrane domain. The predicted membrane organization is similar to that of α-, β-, and γ-sarcoglycan, all of them having single transmembrane domains, large extracellular and small intracellular domains. Furthermore, the amino acid sequence is about 60% identical to γ-sarcoglycan, suggesting a similarity in function for these proteins. No significant homologies to other previously characterized proteins or domains were found in the databases.

| Amino Acid Sequence | Position in γ-SG | Position in δ-SG |
|---|---|---|
| EQYLTATE (SEQ ID NO: 4) | 3–11 | |
| DGLILEGES (SEQ ID NO: 5) | 76–84 | |
| LKVGPQXVEVQSQQXQINS (SEQ ID NO: 6) | 126–144 | |
| SLFTVDEEEVVVGTDRL (SEQ ID NO: 7) | 148–165 | |
| VTGPEGALFEHSVETPLV (SEQ ID NO: 8) | 167–184 | |
| SLSMDAP (SEQ ID NO: 9) | 200–207 | |
| LVQGTQAASG (SEQ ID NO: 10) | 248–257 | |
| STMPGSVGPQVYK (SEQ ID NO: 11) | | 12–24 |
| GLKLEGDSEFLQPLYAK (SEQ ID NO: 12) | | 76–92 |
| EIQSRPGNALYFK (SEQ ID NO: 13) | | 93–105 |
| NVTVNILDQTK (SEQ ID NO: 14) | | 109–120 |
| VLTQLITGP (SEQ ID NO: 15) | | 121–129 |
| KFEVK (SEQ ID NO: 16) | | 139–142 |
| LFSADMNNXVVGAFR (SEQ ID NO: 17) | | 149–163 |
| VLGAEGTVFPK (SEQ ID NO: 3) | | 166–176 |

-continued

| Amino Acid Sequence | Position in γ-SG | Position in δ-SG |
|---|---|---|
| IETPNVR (SEQ ID NO: 18) | | 178–184 |
| ADPFKEL (SEQ ID NO: 19) | | 185–191 |
| SLVMEAP (SEQ ID NO: 20) | | 199–205 |
| VEINAEAGNMEA (SEQ ID NO: 21) | | 208–219 |

Tissue Distribution of δ-sarcoglycan mRNA

To determine the tissue distribution of δ-sarcoglycan, Northern blot analysis of RNA from multiple human adult tissues was performed with the full length coding region of δ-sarcoglycan. A predominant transcript of approximately 1.4 kb is detected in skeletal and cardiac muscle. Signals of 4.3, and 9.5 kb were also detected in these tissues when probing with the full length coding region of δ-sarcoglycan. This result suggests the existence of alternatively spliced and/or polyadenylated forms of the message. The expression pattern is similar to that of α- and γ-sarcoglycan transcripts which are only expressed in skeletal and cardiac muscle, but differs from the β-sarcoglycan transcript which is ubiquitously expressed.

Molecular Organization of the Sarcoglycan Complex

To characterize the δ-sarcoglycan protein, polyclonal antibodies were produced against a specific synthetic peptide (amino acids 166–176). This peptide sequence is not conserved entirely in γ-sarcoglycan and likely represents a unique epitope for δ-sarcoglycan in the extracellular domain. To determine the specificity of the affinity-purified anti-δ-sarcoglycan peptide antibodies, glutathione-S-transferase (GST) fusion proteins, containing either the extracellular domain of γ-sarcoglycan (FP-N) or the extracellular domain of δ-sarcoglycan (FP-M) were constructed. These fusion proteins were then tested for reactivity with the affinity-purified anti-δ-sarcoglycan peptide antibodies. Affinity-purified anti-γ-sarcoglycan peptide antibodies stained fusion protein N but not fusion protein M, whereas affinity-purified anti-δ-sarcoglycan peptide antibodies stained fusion protein M but not fusion protein N. In addition, an affinity purified anti FP-M from goat serum immunized with the entire DGC stained both fusion protein N and M. These results confirm the specificity of the antibodies for γ- and δ-sarcoglycan. Furthermore, the fact that affinity purified anti FP-M antibodies react with both fusion protein N and M, demonstrate the sequence homology between γ- and δ-sarcoglycan. The δ-sarcoglycan affinity-purified antibodies reacted on immunoblotting with a single protein band at 35 kDa in rabbit skeletal crude sarcolemmal membranes and purified DGC. The sarcolemmal staining was much weaker than in the purified DGC, indicating an enrichment of δ-sarcoglycan in the DGC. In immunofluorescence studies, affinity-purified anti-peptide antibodies selectively stained the sarcolemma of human skeletal muscle. Skeletal muscle from DMD patients showing a reduction of DGC components also showed reduced sarcolemmal expression of δ-sarcoglycan by immunofluorescence analysis. Thus, enrichment of δ-sarcoglycan in the DGC and its reduction in muscle from DMD patients demonstrated that it is an integral component of the DGC.

It has been previously demonstrated that α-, β-, and γ-sarcoglycan are tightly associated in the sarcolemma and so constitute the sarcoglycan complex within the DGC. The high degree of sequence similarity between γ- and δ-sarcoglycan suggested that the latter may also be a member of the sarcoglycan complex. To address this question, a western blot transfer of the sarcoglycan complex, prepared from a fraction enriched in microsomes, was probed with affinity-purified anti δ-sarcoglycan peptide antibodies. δ-Sarcoglycan was specifically detected in the purified sarcoglycan complex demonstrating its tight association with α-, β- and γ-sarcoglycan.

Similarity in molecular weight between γ- and δ-sarcoglycan has so far rendered these proteins indistinguishable from each other by SDS PAGE. However, as determined by western blot, treatment of purified DGC with endoglycosidase F/PNGase F resulted in a decrease of the apparent molecular weight of γ-sarcoglycan by approximately 2 kDa whereas the apparent molecular weight of δ-sarcoglycan decreased by approximately 3 kDa. Therefore, deglycosylation of γ- and δ-sarcoglycan allows the separation of these two proteins by SDS PAGE. This finding also confirms the N-linked glycosylation of δ-sarcoglycan predicted by sequence analysis and suggests that the discrepancy between the calculated and apparent molecular weights is primarily due to glycosylation. These results demonstrate again the specificity of both γ- and δ-sarcoglycan antibodies. Furthermore, densitometric analysis of Coomassie blue-stained SDS PAGE of endoglycosidase F/PNGase F treated DGC showed the four sarcoglycan proteins to be equal on a stoichiometric basis.

Chromosomal Localization

Figure 1:
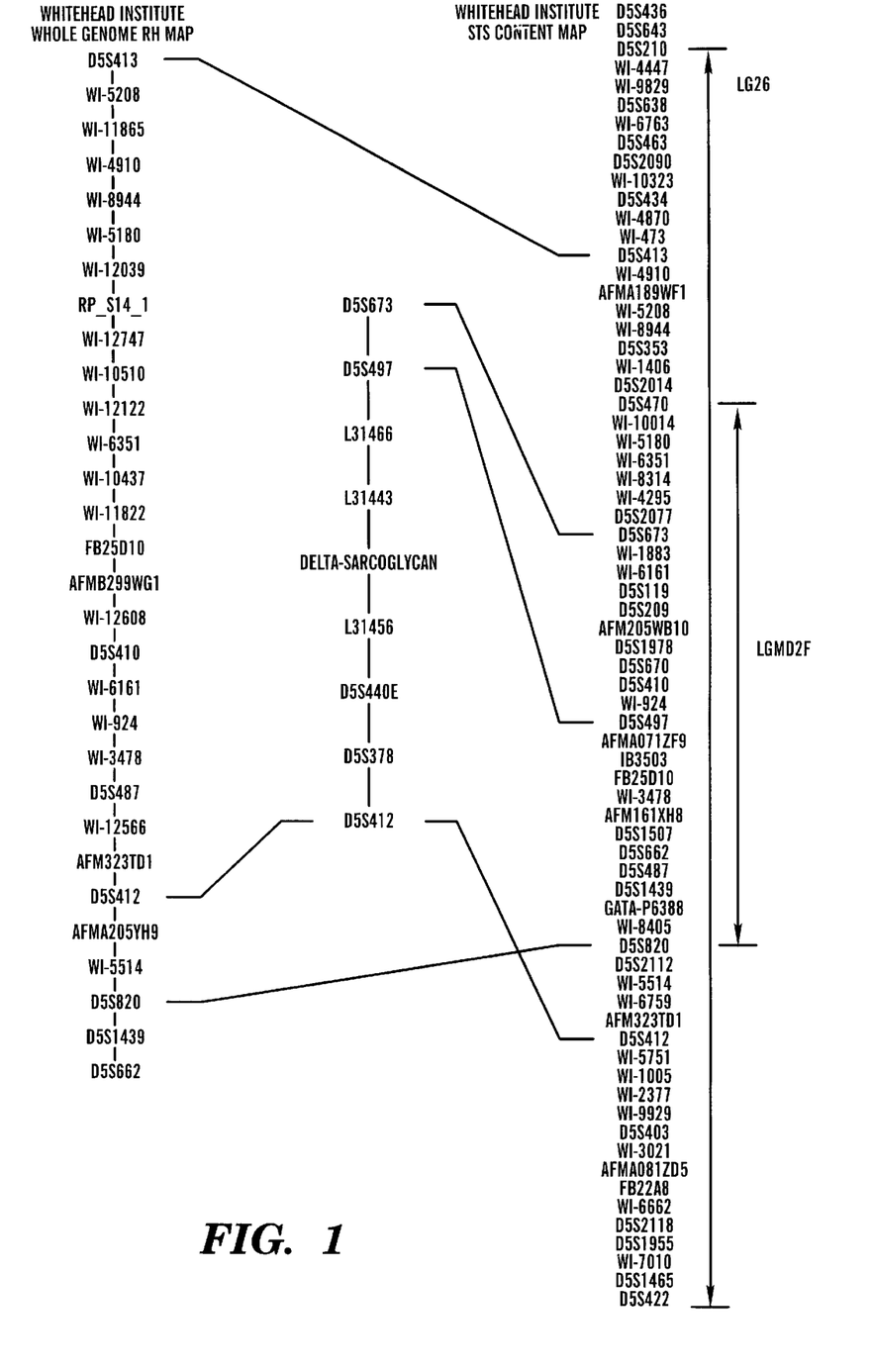

To determine the chromosomal localization of the δ-sarcoglycan gene, primers were designed in order to amplify a fragment of the δ-sarcoglycan gene from a panel of human rodent somatic cell hybrids containing various combinations of human chromosomes. Using this method, the human δ-sarcoglycan gene was assigned to chromosome 5q. To narrow down the chromosomal region, the same process was used to analyze DNA isolated from human rodent somatic cell hybrids containing various fragments of chromosome 5q. The δ-sarcoglycan gene was mapped to 5q31.3–q33.2, a region that overlaps with the candidate interval for autosomal dominant LGMD1A. A radiation hybrid panel was analyzed which allowed precise mapping of the gene between markers D5S497 and D5S378 (FIG. 1 and Table 2). A new form of LGMD has recently been described that is linked to 5q33–q34 (LGMD2F) and mapped between markers D5S470 and D5S820, a region that overlaps the interval defined by markers D5S497 and D5S378 (FIG. 1). The chromosomal localization of the δ-sarcoglycan gene to 5q33–q34 together with the involvement of the other sarcoglycans in LGMDs, makes δ-sarcoglycan a strong candidate for LGMD2F.

| Locus | cR6000 | LOD |
|---|---|---|
| D5S673 | 73.7 | 6.89 |
| D5S497 | 48 | 11.27 |
| L31466 | 43 | 11.19 |
| L31443 | 37.8 | 13.29 |
| L31456 | 20.8 | 19.90 |
| D5S440E | 26.1 | 17.70 |
| D5S378 | 34.0 | 14.52 |
| D5S412 | 51.3 | 10.82 |

Sarcoglycan Complex in LGMD

It has been demonstrated that mutations in α-, β-, or γ-sarcoglycan lead to LGMD, characterized by a marked reduction of the sarcoglycan complex. Since δ-sarcoglycan is a novel member of this complex, we examined the status of this protein in skeletal muscle biopsy specimens from patients with characterized LGMD2C, 2D and 2E. Immunofluorescence analysis revealed an altered expression of δ-sarcoglycan compared to normal human skeletal muscle. Some patients showed absence of the protein whereas in others some sarcolemmal staining was still observed. In addition to a reduced expression of δ-sarcoglycan, those patients also showed a reduction or total loss of the other sarcoglycan proteins. Therefore, a common feature of LGMD2C, 2D and 2E is a specific absence of the sarcoglycan complex at the sarcolemma.

We claim:

1. An isolated nucleic acid molecule encoding the amino acid sequence shown in SEQ ID NO: 2.

2. An isolated nucleic acid molecule which is fully complementary to an isolated nucleic acid molecule encoding the amino acid sequence shown in SEQ ID NO: 2.

3. An isolated nucleic acid sequence comprising SEQ ID NO: 1.

4. A DNA expression construct comprising a nucleic acid molecule encoding the amino acid sequence shown in SEQ ID NO:2.

5. A prokaryotic cell transformed with a DNA expression construct comprising a nucleic acid molecule encoding the amino acid sequence shown in SEQ ID NO:2.

6. A eukaryotic cell transformed with a DNA expression construct comprising a nucleic acid molecule encoding the amino acid sequence shown in SEQ ID NO:2.

* * * * *